(12) United States Patent
Nabutovsky et al.

(10) Patent No.: US 9,301,713 B2
(45) Date of Patent: Apr. 5, 2016

(54) METHOD AND SYSTEM TO ASSESS MECHANICAL DYSSYNCHRONY BASED ON MOTION DATA COLLECTED BY A NAVIGATION SYSTEM

(71) Applicant: Pacesetter, inc., Sunnyvale, CA (US)

(72) Inventors: Yelena Nabutovsky, Mountain View, CA (US); Hoda Razavi, San Jose, CA (US); Kyungmoo Ryu, Palmdale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/328,523

(22) Filed: Jul. 10, 2014

(65) Prior Publication Data

US 2015/0133802 A1 May 14, 2015

Related U.S. Application Data

(60) Provisional application No. 61/906,311, filed on Nov. 19, 2013, provisional application No. 61/906,300, filed on Nov. 19, 2013, provisional application No. 61/906,305, filed on Nov. 19, 2013.

(51) Int. Cl.
*A61B 5/02* (2006.01)
*A61B 5/11* (2006.01)
(Continued)

(52) U.S. Cl.
CPC .............. *A61B 5/1128* (2013.01); *A61B 5/0245* (2013.01); *A61B 5/4836* (2013.01);
(Continued)

(58) Field of Classification Search
CPC .............. A61B 5/02405; A61B 5/0245; A61B 5/1128; A61B 5/4836; A61B 5/742; A61B 6/032; A61B 6/503; A61B 2576/023; A61B 6/487
See application file for complete search history.

(56) References Cited

U.S. PATENT DOCUMENTS 5,391,199 A  2/1995 Ben-Haim
6,233,476 B1  5/2001 Strommer et al.
(Continued)

FOREIGN PATENT DOCUMENTS

EP  1 070 480 A2  1/2001
EP  1 508 300 A1  2/2005
(Continued)

OTHER PUBLICATIONS

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
(Continued)

*Primary Examiner* — George Manuel
(74) *Attorney, Agent, or Firm* — Theresa A. Raymer (57) ABSTRACT

A method and system are provided for analyzing motion data collected by a cardiovascular navigation system to determine a level of dyssynchrony exhibited by a heart. The method and system comprise obtaining a motion data (MD) set that includes a plurality of map point specific motion data (PSMD) collections of motion data. The motion data in each PSMD collection includes information indicating an amount and direction of motion that occurred at a corresponding map point on a wall of the heart during a select period of time, such as during at least one cardiac cycle. The method and system divide the PSMD collections of data into sectors which may be associated with corresponding phases of the cardiac cycle, and analyze the sectors of the PSMD collections to determine at least one of a slope, a magnitude and a direction of motion at the corresponding map point of the wall of the heart during the associated sector. The method and system assess at least one of the slope, magnitude and direction of motion occurring at the corresponding map points of the wall, and calculate a measure of dyssynchrony in the map points of the wall based on at least one of i) whether the map points move in a select direction during select sectors, ii) whether the map points move by a select amount during the select sectors, iii) a direction of strain waveform during select phases of the cardiac cycle and/or iv) an extent of strain during the select phases.

19 Claims, 8 Drawing Sheets

(51) Int. Cl.
*A61B 5/00* (2006.01)
*A61B 5/0245* (2006.01)
*A61B 6/03* (2006.01)
*A61B 5/024* (2006.01)
*A61B 6/00* (2006.01)

(52) U.S. Cl.
CPC ............ *A61B 5/742* (2013.01); *A61B 6/032* (2013.01); *A61B 5/02405* (2013.01); *A61B 6/487* (2013.01); *A61B 6/503* (2013.01); *A61B 2576/023* (2013.01)

(56) References Cited

U.S. PATENT DOCUMENTS

| | | |
|---|---|---|
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,397 B2 | 8/2007 | Hauck et al. |
| 7,276,064 B2 | 10/2007 | Paul et al. |
| 7,338,486 B2 | 3/2008 | Sliwa et al. |
| 7,386,339 B2 | 6/2008 | Strommer et al. |
| 7,505,809 B2 | 3/2009 | Strommer et al. |
| 7,697,973 B2 | 4/2010 | Strommer et al. |
| 7,881,769 B2 | 2/2011 | Sobe |
| 8,016,764 B1 | 9/2011 | Shelchuk |
| 2003/0093069 A1 | 5/2003 | Panescu |
| 2003/0233039 A1 | 12/2003 | Shao et al. |
| 2005/0154282 A1 | 7/2005 | Li et al. |
| 2007/0073179 A1 | 3/2007 | Afonso et al. |
| 2007/0100332 A1 | 5/2007 | Paul et al. |
| 2007/0181139 A1 | 8/2007 | Hauck |
| 2007/0244479 A1 | 10/2007 | Beatty et al. |
| 2007/0270705 A1 | 11/2007 | Starks |
| 2008/0009758 A1 | 1/2008 | Voth |
| 2008/0091193 A1 | 4/2008 | Kauphusman et al. |
| 2009/0163904 A1 | 6/2009 | Miller et al. |
| 2009/0171345 A1 | 7/2009 | Miller et al. |
| 2010/0168550 A1 | 7/2010 | Byrd et al. |
| 2011/0208038 A1* | 8/2011 | Konofagou et al. .......... 600/410 |
| 2012/0184863 A1 | 7/2012 | Harlev et al. |
| 2013/0222415 A1 | 8/2013 | Vilsmeier |
| 2013/0272592 A1 | 10/2013 | Eichler et al. |
| 2015/0141765 A1 | 5/2015 | Razavi et al. |
| 2015/0141858 A1 | 5/2015 | Razavi et al. |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

International Search Report and Written Opinion in PCT Application No. PCT/US2015/028206 (Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,731 filed Jun. 30, 1998 for "Chamber Mapping System".
Advisory Action mailed Aug. 10, 2015; Related U.S. Appl. No. 12/347,216.
Amendment filed Jun. 25, 2015; Related U.S. Appl. No. 12/347,216.
Final Office Action mailed May 4, 2015; Related U.S. Appl. No. 12/347,216.
Amendment filed Dec. 18, 2014; Related U.S. Appl. No. 12/347,216.
Non-Final Office Action mailed Oct. 2, 2014; Related U.S. Appl. No. 12/347,216.
Advisory Action mailed May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action mailed Feb. 25, 2014; Related U.S. Appl. No. 12/347,216.
Amendment filed Feb. 4, 2014; Related U.S. Appl. No. 12/347,216.
Non-Final Office Action mailed Nov. 21, 2013; Related U.S. Appl. No. 12/347,216.
Amendment filed Oct. 29, 2012; Related U.S. Appl. No. 12/347,216.
Advisory Action mailed Oct. 11, 2012; Related U.S. Appl. No. 12/347,216.
Amendment filed Oct. 1, 2012; Related U.S. Appl. No. 12/347,216.
Advisory Action mailed Sep. 12, 2012; Related U.S. Appl. No. 12/347,216.
Amendment filed Aug. 28, 2012; Related U.S. Appl. No. 12/347,216.
Final Office Action mailed Jun. 29, 2012; Related U.S. Appl. No. 12/347,216.
Amendment filed May 14, 2012; Related U.S. Appl. No. 12/347,216.
Interview Summary, Feb. 28, 2012; Related U.S. Appl. No. 12/347,216.
Non-Final Office Action mailed Feb. 13, 2012; Related U.S. Appl. No. 12/347,216.

\* cited by examiner

METHOD AND SYSTEM TO ASSESS MECHANICAL DYSSYNCHRONY BASED ON MOTION DATA COLLECTED BY A NAVIGATION SYSTEM

RELATED APPLICATION DATA

The present application is related to and claims priority from the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD AND SYSTEM TO ASSESS MECHANICAL DYSSYNCHRONY BASED ON MOTION DATA COLLECTED BY A NAVIGATION SYSTEM", all of which are expressly incorporated herein by reference in their entirety.

BACKGROUND OF THE INVENTION

Embodiments of the present disclosure generally relate to methods and systems for determining a level of mechanical dyssynchrony in the heart.

A prevailing theory regarding response to cardiac resynchronization therapy (CRT) is that the therapy corrects mechanical dyssynchrony of the heart. Therefore, methods and systems have been proposed to accurately assess the dyssynchrony. The dyssynchrony information can be used to predict response to CRT as well as optimize LV lead placement and CRT programming parameters. Today, most methods to assess mechanical dyssynchrony involve echocardiography. However, in certain circumstances, conventional echocardiography techniques may experience errors that lead to inaccurate characterization of dyssynchrony. Further, questions still remain as to which specific approach(es) are preferred for assessing dyssynchrony, with various indices being used with mixed success.

Today, various cardiovascular navigation systems exist. For example, the St. Jude Medical MediGuide™ (MDG) cardiovascular navigation system is a 3-D electromagnetic navigation system that provides real-time position and orientation information regarding sensors embedded in electrophysiologic tools. The MDG system is integrated with a fluoroscopic (or other diagnostic) imaging system and tracks the sensors continuously within an imaging volume defined by the fluoroscopic system, on both live and recorded background diagnostic images.

Recently, it has been proposed to utilize the MDG system to characterize motion of the heart and to identify a desired (e.g., optimal) location for placement of a left ventricular (LV) lead. For example, the MDG system systematically records information associated with various endocardial and epicardial locations in the LV. Depending on the size of the heart and other factors during the procedure, there may be between 40 and 120 endocardial LV locations and/or a multitude of epicardial locations at which the MDG system obtains motion recordings for each patient. These recordings then need to be analyzed to characterize motion and mechanical activation patterns in the LV.

A need exists for methods and systems that utilize cardiovascular navigation systems for assessing mechanical dyssynchrony in connection with determining lead placement and programming parameters.

SUMMARY

In accordance with embodiments herein, a method and system are provided for analyzing motion data collected by a cardiovascular navigation system to determine a level of mechanical dyssynchrony exhibited by various map points of the heart. The method and system obtain a motion data (MD) set that includes a plurality of map point specific motion data (PSMD) collections of motion data. The motion data in each PSMD collection includes information indicating an amount and/or direction of motion that occurred at a corresponding map point location on a wall of the heart during at least one cardiac cycle. The method and system divide the PSMD collections of data into sectors associated with corresponding phases of the cardiac cycle, and analyze the sectors of the PSMD collections to determine at least one of a magnitude and a direction of motion at the corresponding map point of the heart wall during the associated phases of the cardiac cycle. The method and system assess at least one of the magnitude and direction of motion occurring at the corresponding map points of the wall during at least a portion of the phases of the cardiac cycle, and calculate a measure of mechanical dyssynchrony exhibited by the map points of the wall based on at least one of i) whether the map points move in a select direction during select phases of the cardiac cycle; ii) whether the map points move by a select amount during the select phases; iii) a direction of strain waveform (increasing or decreasing) during select phases of the cardiac cycle and/or iv) an extent of strain during the select phases.

Embodiments herein are intended to assess dyssynchrony for the entire heart, with motion waveforms being recorded at map points that are evenly or unevenly distributed throughout the heart over multiple chamber walls. A dyssynchrony score may be a global score. Optionally, averaging waveforms may be used for each map point when comparing direction and extent of motion between map points, for example between map points located on opposite heart walls.

Optionally, the calculating operation may determine a proportion of the map points that are moving in the select direction which represents at least one of inward during a systole phase and outward during a diastole phase. Optionally, the calculating operation may include calculating, as the measure, a proportion of a number of map points that move in the select direction out of a total number of map points. Optionally, the calculation may calculate a proportion between total area and area portion that is moving in a select direction. In this example, when a select number of points are encompassed within a select area on the heart, the method calculates the proportion of the total surface area of the heart that this select area encompasses.

BRIEF DESCRIPTION OF THE DRAWINGS

FIG. 5A illustrates an example of a display window that may be presented to one or more users on a workstation, imaging system, laptop computer, smart phone, mobile handheld devices and the like.

FIG. 5B illustrates an example of a display window that may be presented to one or more users on a workstation, imaging system, laptop computer, smart phone, mobile handheld devices and the like.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Embodiments herein may be implemented with, and/or utilize aspects of, the methods and system described in the following co-pending applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. patent application Ser. No. 14/270,181 titled "METHOD AND SYSTEM TO CHARACTERIZE MOTION DATA BASED ON NEIGHBORING MAP POINTS", which is filed on or about the same day as the present application, U.S. patent application Ser. No. 14/270,186 titled "METHOD AND SYSTEM FOR CALCULATING STRAIN FROM CHARACTERIZATION DATA OF A CARDIAC CHAMBER", which is filed on or about the same day as the present application, U.S. patent application Ser. No. 14/270,176 titled "METHOD AND SYSTEM FOR DISPLAYING A THREE DIMENSIONAL VISUALIZATION OF CARDIAC MOTION", which is filed on or about the same day as the present application, all of which are expressly incorporated herein by reference in their entirety.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM. EEPROM, flash drive, or the like), such as software, and/or that operate based on instructions that are hardwired into the logic of the device.

At least one technical effect of at least one portion of the methods and systems described herein includes i) analyzing motion data collected by a cardiovascular navigation system to determine a level of dyssynchrony exhibited by a heart; ii) obtaining a motion data (MD) set that includes a plurality of map point specific motion data (PSMD) collections of motion data, wherein the motion data in each PSMD collection includes information indicating an amount of motion and direction of motion that occurred at a corresponding map point location on a wall of the heart during at least one cardiac cycle; iii) dividing the PSMD collections of data into sectors associated with corresponding phases of the cardiac cycle; iv) analyzing the sectors of the PSMD collections to determine at least one of a magnitude and a direction of motion at the corresponding map point of the wall of the heart during the associated phases of the cardiac cycle; v) assessing at least one of the magnitude and direction of motion occurring at the corresponding map points of the wall; and vi) calculating a measure of dyssynchrony in the map points of the wall based on at least one of i) whether the map points move in a select direction during select phases of the cardiac cycle; ii) whether the map points move by a select amount during the select phases; iii) a direction of strain waveform (increasing or decreasing) during select phases of the cardiac cycle and/or iv) an extent of strain during the select phases.

Figure 1A:
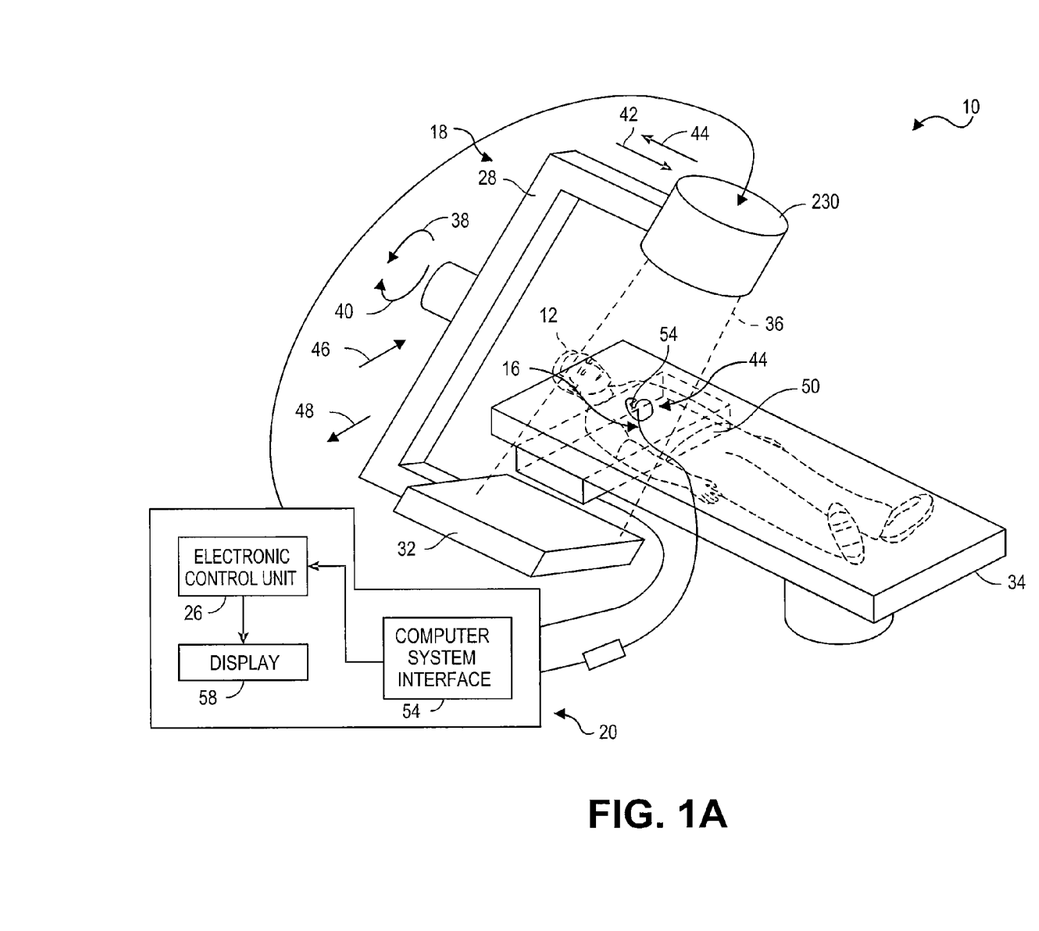
FIG. 1A illustrates an imaging and navigation system for use in imaging an anatomical region of the heart and to collect motion data in connection with embodiments herein.

FIG. 1A illustrates an imaging and navigation system 10 for use in imaging an anatomical region of a patient 12 such as a heart 14. Optionally, the imaging equipment may be removed entirely. A medical tool 16 is implanted within the anatomical region, such as for example, an electrophysiological (EP) mapping catheter or a catheter generally described or shown in U.S. Pat. No. 7,881,769, the entire disclosure of which is incorporated herein by reference. The medical tool 16 includes a plurality of electrophysiological sensors 52 that may be placed on the endocardial or epicardial surface of the left ventricle of the heart 14. The electrophysiological sensors 52 may be attached to the distal or proximal end of the medical tool 16, or any point in between. The electrophysiological sensors 52 measure a position and an electrical potential or an electric current of biological cells and tissues, and are transmitted to an electronic control unit (ECU) 26. For example, the electrophysiological sensors 52 may be positioned by the medical tool 16 to measure the electrical potential along a portion of the wall of the heart 14. It should be understood, however, that the electrophysiological sensors 52 could be used in a variety of anatomical regions within the heart 14 or other organs in which motion characterization may be of interest.

System 10 may include an imaging system 18 and a medical device navigation system 20. The system 10 may also include a registration system for registering a group of images of the anatomical region of patient 12 in a navigation coordinate system of the navigation system 20 as generally described and shown in U.S. Patent Publication 2013/

0272592 and International Pub. No. WO 2012090148, the entire disclosures of which are incorporated herein by reference.

The imaging system 18 is provided to acquire images of heart 14 or another anatomical region of interest and comprises a fluoroscopic imaging system in the illustrated embodiment. Although a fluoroscopic imaging system is described in this embodiment, the embodiments described herein may find use with other types of imaging systems, for example, but without limitation, computed tomography (CT) imaging systems and three-dimensional radio angiography (3DRA) systems. System 18 may include a C-arm support structure 28, a radiation emitter 30, and a radiation detector 32. Emitter 30 and detector 32 are disposed on opposite ends of support structure 28 and disposed on opposite sides of patient 12 as patient 12 lays on an operation table 34. Emitter 30 and detector 32 define a field of view 36 and are positioned such that the field of view 36 includes the anatomical region of interest as patient 12 lays on operation table 34. Imaging system 18 is configured to capture images of anatomical features and other objects within field of view 36. Support structure 28 may have freedom to rotate about the patient as shown by lines 38, 40. Support structure 28 may also have freedom to slide along lines 42, 44 (i.e. along the cranio-caudal axis of patient 12) and/or along lines 46, 48 (i.e. perpendicular to the cranio-caudal axis of patient 12). Rotational and translational movement of support structure 28 yields corresponding rotational and translational movement of field of view 36.

Imaging system 18 may acquire a group of images of an anatomical region of patient 12 by first shifting along lines 42, 44, 46, 48 to place the anatomical region of interest within the field of view 36. Second, support structure 23 may rotate radiation emitter 30 and radiation detector 32 about patient 12, keeping the anatomical region within field of view 36. Imaging system 18 may capture images of the anatomical region as support structure 28 rotates, providing a group of two-dimensional images of the anatomical region from a variety of angles. The group of images may be communicated to ECU 26 for image processing and display. The group of images may comprise a sequence of images taken over a predetermined time period.

Navigation system 20 is provided to determine the position of medical tool 16 within the body of patient 12 and to permit a clinician to navigate tool 16 within the body. In the illustrated embodiment, system 20 comprises a magnetic navigation system in which magnetic fields are generated in the anatomical region and position sensors associated with tool 16 generate an output that changes responsive to the position of the sensors within the magnetic field. System 20 may comprise, for example, the systems generally shown and described in, for example, U.S. Pat. Nos. 6,233,476, 7,197, 354, 7,386,339, and 7,505,809 all of which are incorporated by reference in their entirety. Although a magnetic navigation system is shown in the illustrated embodiment, it should be understood that the invention could find use with a variety of navigation systems including those based on the creation and detection of axes specific electric fields. Navigation system 20 may include a transmitter assembly 50.

The transmitter assembly 50 is conventional in the art and may include a plurality of coils arranged orthogonally to one another to produce a magnetic field in and/or around the anatomical region of interest. It should be noted that, although transmitter assembly 50 is shown under the body of patient 12 and under table 34 in FIG. 5, transmitter assembly 50 may be placed in another location, such as attached to radiation emitter 30, from which the magnetic field generators can project a magnetic field in the anatomical region of interest. In accordance with certain embodiments of the invention the transmitter assembly 50 is within the field of view 36. The ECU 26 may control the generation of magnetic fields by transmitter assembly 50.

The electrophysiological sensors 52 are configured to generate an output dependent on the relative position of electrophysiological sensors 52 within the field generated by transmitter assembly 50. In FIG. 1A, the electrophysiological sensor 52 and medical tool 16 are shown disposed around the heart 14. As medical tool 16 is guided to and through the region of interest, the navigation system 20 determines the location of the electrophysiological sensors 52 in the generated field, and thus the position of medical tool 16 as well. The tool 16 may be guided to endocardial locations and/or epicardial locations, to collect motion data. The navigation system 20 further determines a navigation coordinate of the navigation coordinate system.

Additionally or alternatively, the motion waveform of the PS motion at a select map point may represent a waveform indicative of strain (e.g., tissue deformation) or strain rate at the select map point from a beginning to an end of a cardiac cycle. Strain is a measure of tissue deformation, and is defined as the change in distance between two points (linear strain) or change in an area (area strain) or volume (volume strain) formed by 3 or more points, normalized to the original distance, area, or volume. There may be three primary directions of strain in the heart: a longitudinal direction, a radial direction, and/or a circumferential direction. Strain rate is the rate at which the tissue deformation or strain occurs. Strain rate may be measured as the time derivative of the linear, area, or volume strain.

For example, the ECU 26 may set a position reference point at the beginning of the cardiac cycle. During the cardiac cycle, the ECU 26 may compare instantaneous positions of the tool 16 at the map point, over the cardiac cycle, against the positions of surrounding map points to acquire the PS motion data representing strain of the map point. The PS motion data may define the strain over the cardiac cycle. Optionally, the ECU 26 may determine the strain rate of the map point by calculating the derivative or change in the strain over time. The strain or strain rate at a select map point may be relative to one or more other map points. Optionally, the select map point may have multiple strains or strain rates associated therewith.

One or more patient reference sensors (not shown) are on the body of the patient 12, for example, on the chest. The patient reference sensors measure a displacement and orientation of the patient reference sensors relative to a predetermined reference point, such as, the electrophysiological sensors 52 or the transmitter assembly 50.

The ECU 26 of the navigation system 20 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 26 may receive a plurality of input signals including signals generated by medical tool 16, imaging system 18, the electrophysiological sensors 52, an operator system interface 54, and the patient reference sensors and generate a plurality of output signals including those used to control tool 16, imaging system 18, the display 58. ECU 26 may also receive an input signal from an organ monitor (not shown), such as an ECG monitor, and sort or segregate images from imaging system 18 based on a timing signal of a monitored organ. For example, ECU 26 may sort images based on the phase of the patient's cardiac cycle at which each image was collected, as more fully described in U.S. Pat. No. 7,697,973, which is hereby incorporated by reference in its entirety.

Figure 1B:
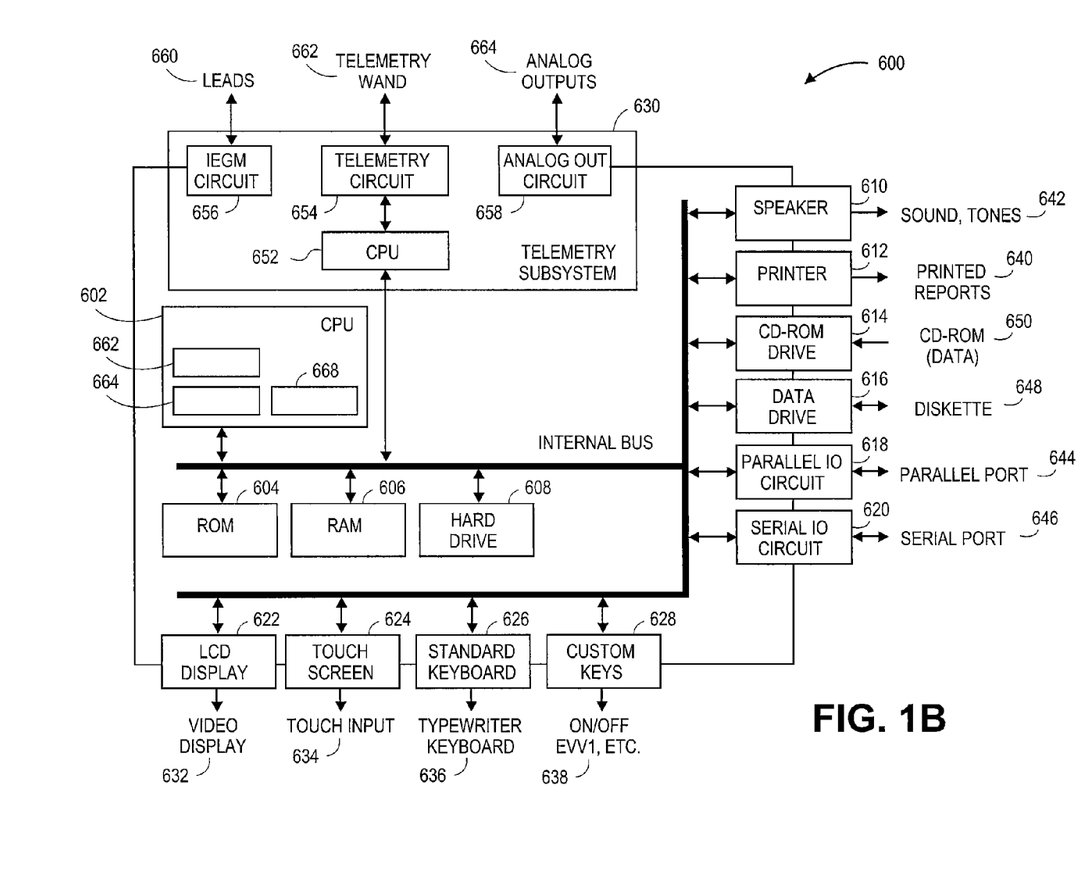
FIG. 1B illustrates a system for analyzing motion data in accordance with embodiments herein.

FIG. 1B illustrates a functional block diagram of an external device 600 that is operated in accordance with the processes described herein to analyze motion data and to interface with users and with implantable medical devices. The external device 600 may be a workstation, a portable computer, an IMD programmer, a PDA, a cell phone and the like. The external device 600 includes an internal bus that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 typically includes a microprocessor, a microcontroller, or equivalent control circuitry, designed specifically to control interfacing with the external device 600 and with the IMD 100. The CPU 602 performs the COI measurement process discussed above. The CPU 602 may include RAM or ROM memory, logic and timing circuitry, state machine circuitry, and I/O circuitry to interface with the IMD 100. The display 622 (e.g., may be connected to the video display 632). The touch screen 624 may display graphic information relating to the IMD 100. The display 622 displays various information related to the processes described herein. The touch screen 624 accepts a user's touch input 634 when selections are made. The keyboard 626 (e.g., a typewriter keyboard 636) allows the user to enter data to the displayed fields, as well as interlace with the telemetry subsystem 630. Furthermore, custom keys 628 turn on/off 638 (e.g., EVVI) the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The CPU 602 is configured to analyze motion data collected by the cardiovascular navigation system to determine a level of mechanical dyssynchrony exhibited by a heart. The CPU 602 receives access to motion data (MD) sets, as explained herein. The CPU 602 includes an PSMD collection analysis circuit module 663 that divides the PSMD collections of data into sectors associated with corresponding phases of the cardiac cycle. The CPU 602 includes an analysis circuit module 665 that analyzes the sectors of the PSMD collections to determine at least one of a magnitude and a direction of motion at the corresponding map point of the wall of the heart during the associated phases of the cardiac cycle. The analysis circuit module 665 assesses at least one of the magnitude and direction of motion occurring at the corresponding map points of the wall. The analysis circuit module 665 performs the assessment during at least a portion of the phases of the cardiac cycle.

A dyssynchrony measure circuit module 668 calculates a measure of mechanical dyssynchrony associated with the map points of the wall based on at least one of i) whether the map points move in a select direction during select phases of the cardiac cycle; ii) whether the map points move by a select amount during the select phases; iii) a direction of strain waveform (increasing or decreasing) during select phases of the cardiac cycle and/or iv) an extent of strain during the select phases. Optionally, the calculation may calculate a proportion between total area and area portion that is moving in a select direction. In this example, when a select number of points are encompassed within a select area on the heart, the method calculates the proportion of the total surface area of the heart that this select area encompasses.

As one example, the measure circuit module 668 may determine, as the measure of dyssynchrony, a proportion of the map points (out of a global set of map points, out of all map points in a corresponding segment and the like) that are moving in the select direction. For example, the select direction may represent at least one of inward during a systole phase and outward during a diastole phase. As another example, the measure circuit module 668 may calculate, as the measure, a percentage of a number of map points that move in the select direction out of a total (global or within a common segment) number of map points. Optionally, the measure circuit module 668 may calculate a proportion between total area and area portion that is moving in a select direction. In this example, when a select number of points are encompassed within a select area on the heart, the method calculates the proportion of the total surface area of the heart that this select area encompasses.

The display 622 displays a dyssynchrony score based on the measure of dyssynchrony in connection with at least one of lead placement for a cardiac resynchronization therapy (CRT) device or programming optimization for a CRT device. The dyssynchrony score may be presented as a numeric value, a color according to a color coded score range, a graph, a word (e.g., high, medium, low) and the like.

The telemetry subsystem 630 includes a central processing unit (CPU) 652 in electrical communication with a telemetry circuit 654, which communicates with both an IEGM circuit 656 and an analog out circuit 658. The circuit 656 may be connected to leads 660. The circuit 656 receives and processes IEGM cardiac signals.

The telemetry circuit 654 is connected to a telemetry wand 662. The analog out circuit 658 includes communication circuits to communicate with analog outputs 664. The external device 600 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hardwired connection may be used to connect the external device 600 to the IMD.

Figure 1C:
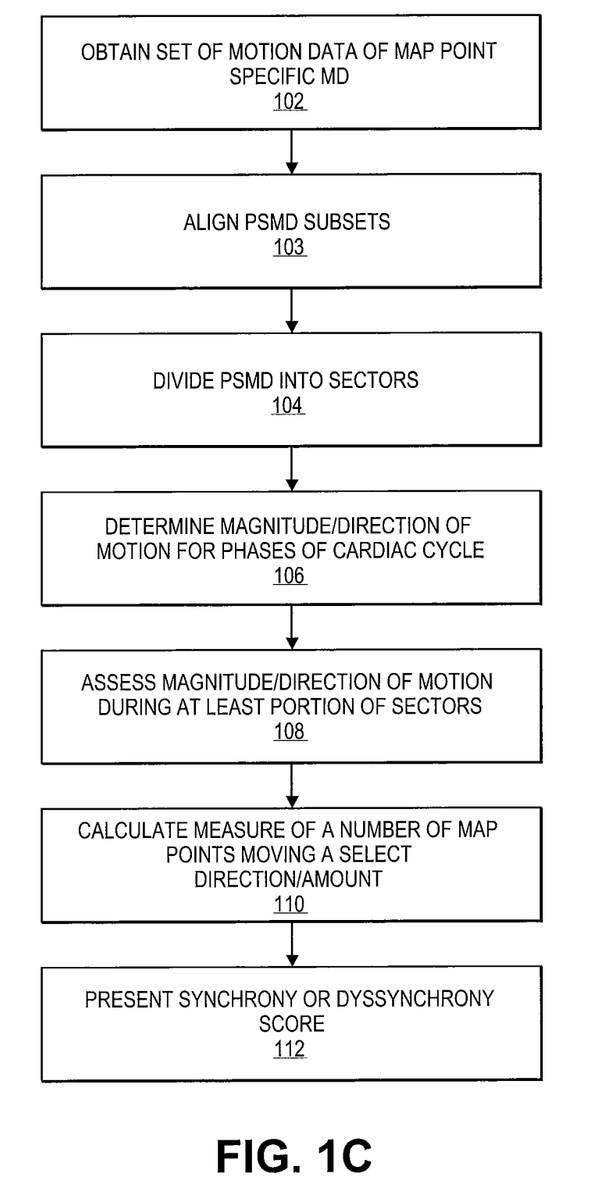
FIG. 1C illustrates a method for analyzing motion data collected by a cardiovascular navigation system to determine a level of dyssynchrony exhibited by the heart in accordance with embodiments herein.

FIG. 1C illustrates a method for analyzing motion data collected by a cardiovascular navigation system 10 to determine a level of dyssynchrony exhibited by the heart.

Beginning at 102, the method obtains a motion data (MD) set that includes a plurality of map point specific motion data (PSMD) collections of motion data. The motion data may be acquired in real-time intra-operatively, or pre-acquired and saved in a data storage that is later accessed at 102. The motion data in each PSMD collection includes information indicating an amount of motion that occurred at a corresponding map point location on a wall of the heart during a select time period such as during at least one cardiac cycle. The heart may be divided into numerous map points along the walls of the various chambers.

Figure 2A:
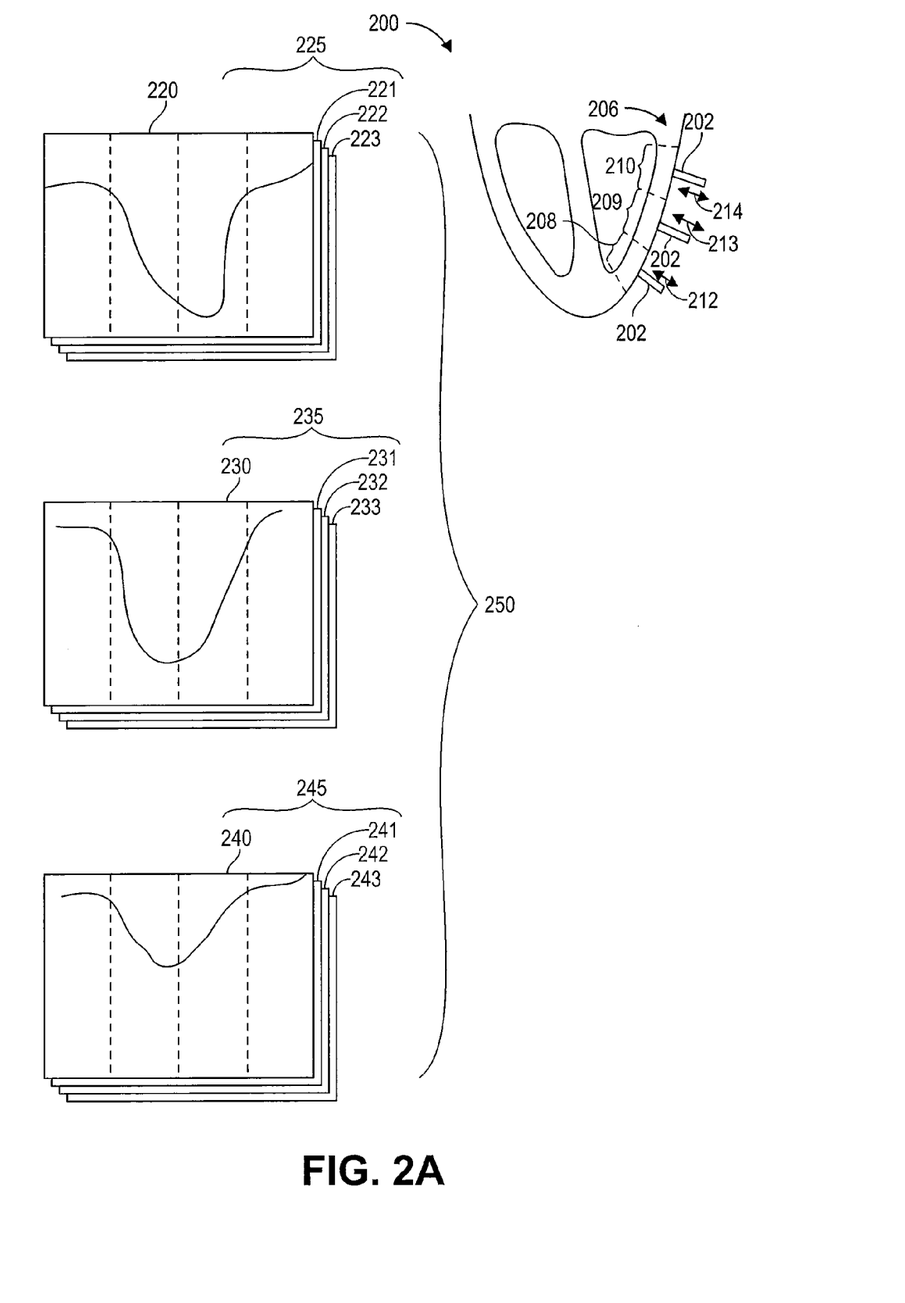
FIG. 2A illustrates a graphical representation of the process of FIG. 1C.

FIG. 2A illustrates a graphical representation of the process of FIG. 1C. FIG. 2A illustrates a portion of a heart 200 having a heart wall 206, for which it is desirable to measure motion and determine synchronous or non-synchronous mechanical behavior. The heart wall 206 may be separated into map points of interest 208-210. The example of FIG. 2A shows three map points of interest 208-210 along the wall of the left ventricle. Optionally more or fewer map points of interest may be designated. A tool 202 (e.g., a catheter, electrophysiology sensor) is positioned directly against the heart wall at one or more points within each map point of interest 208-210. In the example of FIG. 2, the tool 202 is shown positioned against a point of interest for each map point 208-210 at different points in time. For example, the tool 202 is positioned, during a first measuring operation, at map point 208 while collecting motion data associated with movement (e.g., along the arrow 212) at the map point 208. The movement may be in various linear, transverse, or rotational directions. Next, the tool 202 may be positioned, during a second measuring operation, at map point 209 while collecting motion data associated with movement (e.g., along the arrow 213) at the map point 209. Next, the tool 202 is positioned, during a third measuring operation, at map point 210 while collecting motion data associated with movement (e.g., along the arrow 214) at the map point 210.

The position of the tool 202 is continuously monitored by the navigation system to obtain sets of motion data associated with each map point 208-210. Returning to the method of FIG. 1C, at 102, a map point specific motion data (PSMD) collection is obtained for at least one cardiac cycle. In FIG. 2, a PSMD collection 220 is collected during one cardiac cycle while the tool 202 is held against the LV wall at map point 208. The tool 202 is held against the LV wall at map point 208 for multiple heart beats thereby generating multiple PSMD collections 220-223 (e.g., for 4 consecutive heart beats). Optionally, PSMD collections may be collected for more than 4 heart beats. The PSMD collections 220-223 associated with map point 208 may be grouped to form a collection 225 of PSMD collections 220-223 associated with a single map point 208.

Once a desired amount of motion data is collected for map point 208, the tool 202 is moved to a next desired position, such as map point 209. Next, the data collection process is repeated to obtain PSMD collections 230-233 that include motion data indicative of an amount and direction of motion experienced by map point 209 over a corresponding number of heart beats (e.g., cardiac cycles). Once a desired amount of motion data is collected for map point 209, the tool 202 is moved to a next desired position such as at map point 210. Next, the data collection process is repeated to obtain PSMD collections 240-243 that include motion data indicative of an amount and direction of motion experienced by map point 210 over a corresponding number of heart beats (e.g., cardiac cycles). The PSMD collections 230-233 and 240-243, that are associated with map points 209 and 210, may be grouped to form collections 235 and 245, respectively, associated with single map points 209 and 210. The plurality of PSMD collections 220-243 for all heart wall map points of interest collectively defines a motion data set 250.

Optionally, multiple tools 202 or a tool with multiple independently movable position sensors may be used to simultaneously collect motion data for multiple map points. Optionally, more map points of the heart wall may be studied to collect additional PSMD collections of motion data. For example, the walls of the RV, RA, and/or LA may also be divided into map points, for which motion data are collected.

The cardiovascular navigation system 10 collects the motion data from one or more tools 202. The tool(s) 202 may be held in contact with the epicardial wall and/or endocardial wall of the heart. The motion data 250 are preprocessed to compensate for changes in tool 202 position, such as due to movement of the imaging equipment (e.g., c-arm movement), due to patient movement, and/or due to respiration. The motion data 250 may be converted to patient-specific cardiac coordinates. The motion data 250 may be analyzed to identify and remove non-ectopic beats and to eliminate beats with abrupt mechanical movement. Optionally, the motion data 250 may include averages of motion data collected over multiple heart beats (cardiac cycles). For example, the PSMD collections 220-223 may be combined through averaging or otherwise. Optionally, the motion data 250, that is utilized in connection with embodiments described hereafter, may include information indicative of a radial component of wall movement, and/or may include information indicative of a longitudinal component of wall movement. Optionally, the motion data may include information associated with 3-dimensional movement calculated as a 3-D distance from an initial position at a select starting point in the cardiac cycle, such as the R wave or local electrical activation time.

Figure 2B:
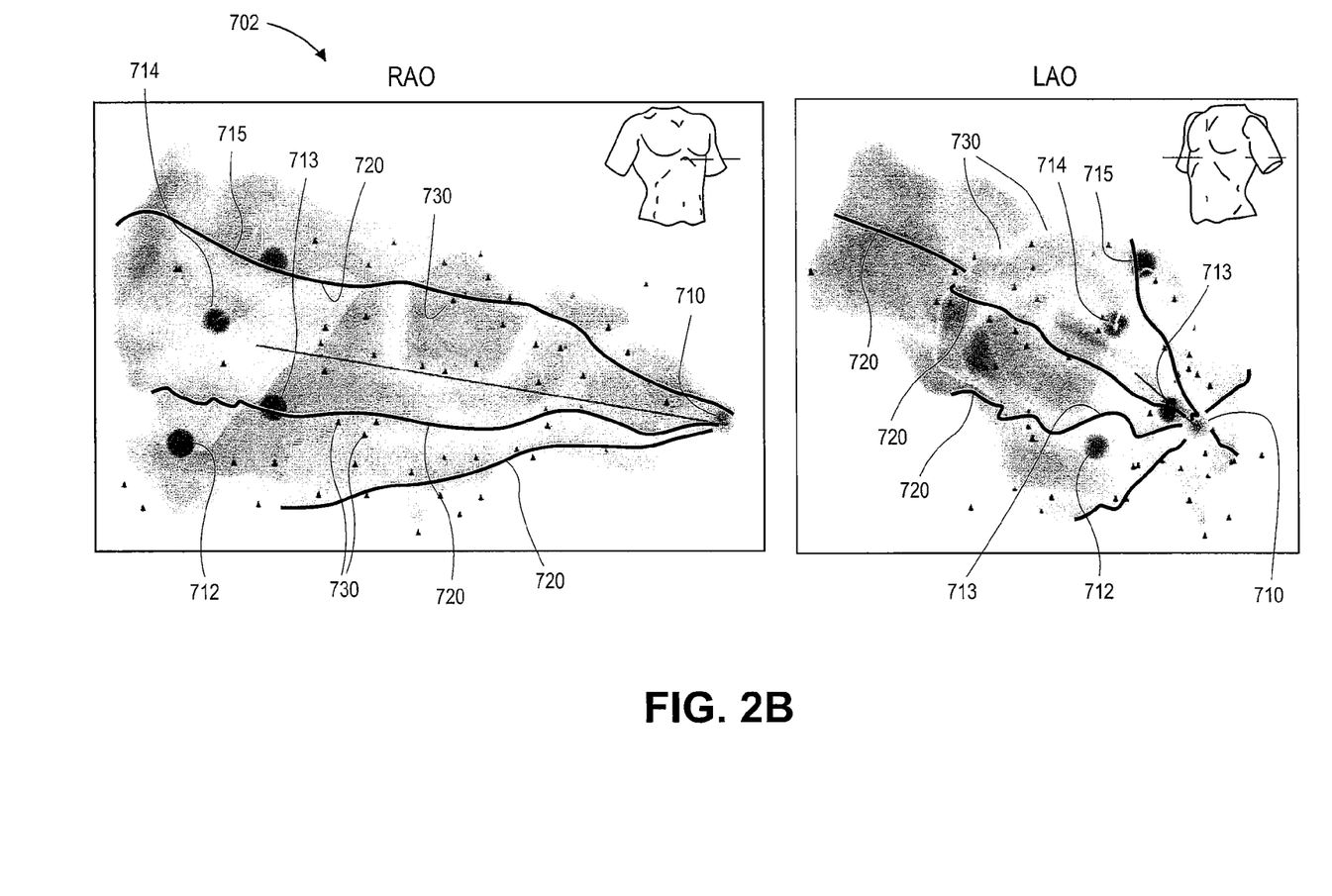
FIG. 2B illustrates examples of graphical representations of at least a portion of the heart that may be presented to a user on a display.

FIG. 2B illustrates examples of graphical representations of at least a portion of the heart that may be presented to a user on a display. By way of example, the user may be presented with graphical depictions of a left ventricle from multiple different views, namely a right anterior oblique (RAO) view 702 and a left anterior oblique (LOA) view 704. The RAO and LAO views 702, 704 may be created, under user control, by the system 10. For example, the system 10 may utilize electro-anatomical mapping to collect surface points on the wall of the heart. As another example, the system 10 may collect imaging data representative of a patient's heart (e.g., MRI, ultrasound, X-ray, CT, PET, SPECT imaging and the like) and process the imaging data to reconstruct one or more 2D or 3D images (e.g., a rendered image, a reconstructed image, and the like).

The system 10 displays one or more electro-anatomical images, selected by the user, and the user designates a collection of patient specific anatomical markers 710, and 712-15 on the displayed images. The anatomical markers 710, 712-715 are defined intra-operatively, in real time, at select points in the cardiac cycle, while the system 10 is collecting imaging data. For example, the user may designate the anatomical marker 710, as a red lesion marker on the electro-anatomical mapping image, to correspond to an apical timestamp. As another example, the user may designate the anatomical markers 712-715, as cyan lesion markers on the electro-anatomical (EA) mapping image, to correspond to the mitral annulus timestamps.

The RAO view 702 and the LAO view 704 illustrate a common geometry for the left ventricle. Optionally, the EA mapping image may include segmentation lines to indicate the segmentation of the LV geometry into a select number of segments. For example, the LV geometry may be divided by six circumferential lines 720 that extend generally in a common direction with a patient specific longitudinal axis. The longitudinal axis may be utilized in connection with performing coordinate transformation of map points in the heart wall to a global or reference coordinate system.

The RAO and LAO views 702, 704 also illustrate a plurality of small triangles 730 located at select locations on the heart wall. The triangles 730 represent the map points at which motion data is collected as described herein. As is evident in FIG. 2B, map points 730 are distributed over a majority of the LV wall in three dimensional space. The map points 730 are unevenly spaced such that groups of map points 730 in select segments are located closer to one another as compared to map points 730 in other segments.

As explained herein, when developing dyssynchrony scores, the scores may be calculated relative to global behavior of map points throughout the entire heart wall. Optionally, the dyssynchrony scores may be calculated relative to chamber specific behavior of map points. For example, direction or extent of motion for map points may be analyzed relative only to map points in a common chamber of the heart. For example, a percentage or proportion of map points having a common systole movement direction or strain direction (and/or extents of movement/strain) may be determined relative to the systole movement or strain direction and/or extent of movement/strain for all considered map points in the same chamber.

Optionally, the dyssynchrony scores may be calculated relative to segment specific behavior of map points. For example, direction or extent of motion or strain for map points may be analyzed relative only to map points in a common segment of the heart. For example, a percentage or proportion of map points having a common systole movement or strain direction (and/or extent of movement/strain) may be determined relative to the systole movement or strain direction and/or extent of movement/strain for all considered map points in the same segment.

Returning to FIG. 1C, the operation at 102 may represent real-time collection of motion data 250 where dyssynchrony scores are supplied on a display to the physician while the tool 202 continues to collect motion data. Alternatively, the motion data 250 may have been previously collected and stored in memory, such as on a network server or hospital database. In this example, the operation at 102 simply accesses the network server or database to read the pre-existing motion data 250 (without real-time motion data collection).

Following the above operations, motion data 250 are now known for each map point of interest along the heart wall. The motion data for any PSMD collection (e.g., 220) may be represented as a corresponding motion waveform representative of movement during a single cardiac beat. For example, the horizontal axis may represent time from the beginning to end of a single heart beat. The vertical axis represents the amount of displacement or position change in the heart wall map point as measured from a start reference position.

It should be recognized that, in certain embodiments, the mapping tool may only collect data for a portion of the heart's endocardial or epicardial surface. For example, when performing epicardial mapping, the method may only collect data for map points along one or more veins that traverse the outside surface of the heart. Motion data may be limited to map points along the coronary sinus vein, its tributaries, the great cardiac vein, the middle cardiac vein and other veins along select anatomical regions.

At 103, the method aligns the PSMD collections of data with one another over a common time interval. When the PSMD collections are collected for periods of time based on the heart rate, the temporal length of each PSMD collection will vary as the heart rate varies. At 103, the method adjusts the PSMD collections of data to extend over a common time interval. For example, the common time interval may be predetermined, or automatically selected, such as by choosing a length corresponding to the longest, shortest, or average length PSMD collection.

The time interval may be set to begin at a point in time defined by a global signal such as the peak of the R-wave as detected by using the Electrocardiogram (ECG) or Intracardiac Electrogram (IEGM) signals. Optionally, the time interval may be defined to begin based on another global marker of electrical activity (e.g., the T-wave, P-wave). The time interval, over which the PSMD collections extend, are equalized such that every PSMD collection defines a local map point motion waveform extending over a common predetermined interval of time. For example, the PSMD collections may be "rotated" as described in the above-identified co-pending provisional applications (Ser. No. 61/910,630 and Ser. No. 61/906,305) to align the motion waveforms between common start and end anchors. During rotation, the motion data points within a motion waveform are adjusted, such as through linear subtraction, based on magnitude differences at a starting anchor (between measured and expected/correct data values) and an ending anchor (between measured and expected/correct data values), as described in the co-pending '630 and '305 provisional applications. Optionally, the PSMD collections may be temporally equalized by "stretching" the waveforms (of PSMD collections) that have shorter cycle lengths until the shorter PSMD collections have a length equal to the predetermined interval. An individual PSMD collection of data may be "stretched" by performing interpolation upon the PSMD collection of measured data to generate synthetic data values for points between the measured data values. Similarly, the PSMD collections, that have longer cycle lengths, may be temporally shortened or shrunk, such as through performing down sampling of the PSMD collection. Alternatively, the waveforms, defined by each PSMD collection, may be cut off at the end of the shortest cycle length.

At 104, the method divides the PSMD collections of data 220-223 into sectors associated with corresponding portions or phases of the cardiac cycle. For example, each heart beat (cardiac cycle) may be divided into phases (e.g., 4 phases). The phases of the cardiac cycle may be defined to correspond to physiologic behavior of interest. Alternatively, the phases may be simply defined as fixed periods of time. For example, each phase may be set to be ¼, ⅒ or some other fraction of a cardiac cycle. The PSMD collections are divided into sectors associated with the phases into which the cardiac cycle is divided.

Figure 3:
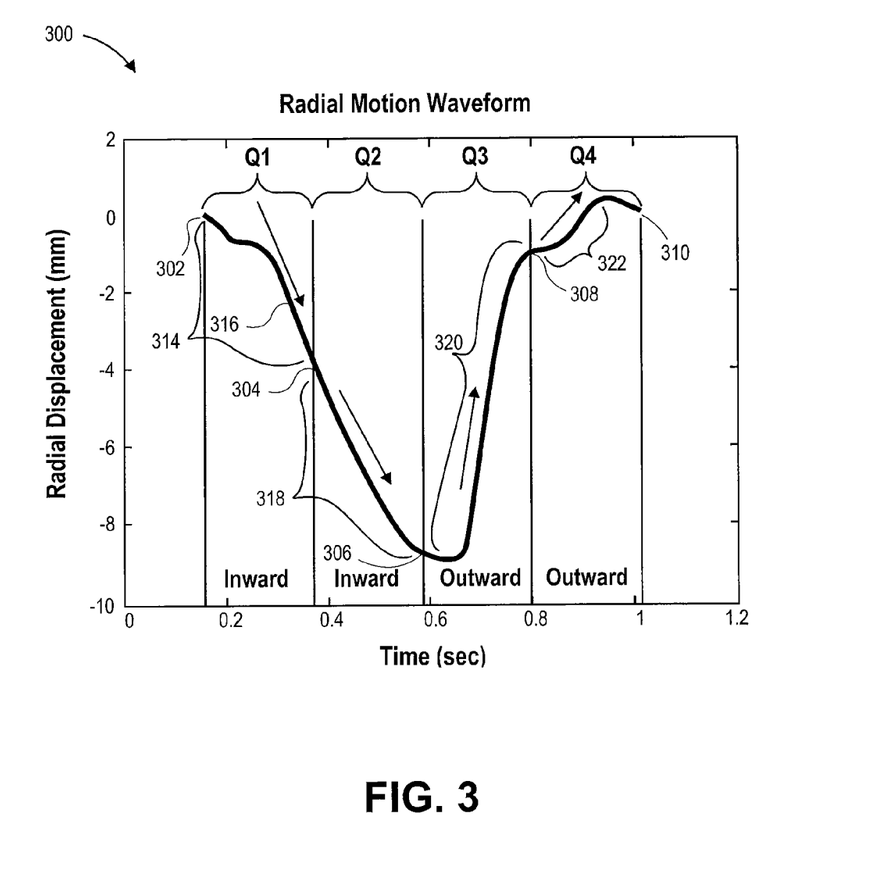
FIG. 3 illustrates a map point specific motion waveform associated with one wall map point and collected during a single cardiac cycle in accordance with embodiments herein.

FIG. 3 illustrates a map point specific motion waveform 300 associated with one wall map point and collected during a single cardiac cycle. The waveform 300 plots radial displacement (e.g., in millimeters) of the map point of interest along the vertical axis and time along the horizontal axis. The direction of movement is illustrated from a beginning/zero point in time until completion of a cardiac cycle (e.g., after 1 sec.). The waveform 300 is divided into sectors Q1-Q4 that are associated with portions or phases of the cardiac cycle. The waveform 300 exhibits an amount of radial motion during each sector Q1-04.

At 106, the method analyzes the sectors Q1-Q4 of the PSMD collections 220-223 to determine at least one of a magnitude and a direction of the longitudinal or radial motion at the corresponding map point on the wall of the heart during the associated portions (e.g., phases) of the cardiac cycle. At 106, the method may analyze a direction of strain waveform during select phases of the cardiac cycle and/or an extent of strain during the select phases. The longitudinal or radial motion may be quantified in terms of the direction of motion and/or the amplitude, magnitude, or extent of motion. Optionally, motion may occur in directions other than radially.

The direction of motion may be inward or outward when representing radial motion. Optionally, the direction of motion may be toward the apex of the heart or away from the apex, when representing longitudinal motion. Regardless of whether the motion is radial or longitudinal, the motion may be characterized as in a direction of contraction (inward or toward the apex) or in a direction of relaxation (outward or away from the apex).

With reference to FIG. 3, the motion may be determined by finding net movement during the sector. For example, in sector Q1 the net movement is determined by identifying a location (displacement) of the first point 302 in the sector Q1 and identifying a location of the last point 304 in the sector Q1. The points 302-310 represent sector transition points and can be compared to determine the net movement and direction in each sector Q1-Q4. For example, in sector Q3, the net movement is approximately 8 mm, as the wall map point moved from a radial displacement of −9.0 at the beginning of sector Q3 to a radial displacement of −1.0 at the end of sector Q3 (corresponding to the beginning of sector Q4).

Alternatively or in addition, the method may analyze the slope of the portion of the waveform 300 in each corresponding sector Q1-Q4. For example, the portion 314 of waveform 300 may have a maximum slope at 316. The method may use the maximum slope to wholly or partially characterize the portion 314. Optionally, the method may calculate the average slope over the length of the sector Q1, and use the average slope to wholly or partially characterize the portion 314. Portions 318-322 are also analyzed to identify maximum and/or average slopes therefore.

At 108, the method assesses at least one of the slope, magnitude direction of motion, strain or strain rate occurring at the corresponding map points of the wall during at least a portion of the sections Q1-Q4 (e.g., phases of the cardiac cycle). For example, the direction of motion may be assessed to determine an indication of a direction of movement (e.g., contraction or relaxation). The sign of the slope may be used as an indication of direction. For example, the waveform portions 314, 318 in sectors Q1 and Q2 exhibit negative average slopes, while the waveform portions 320, 322 in sectors Q3 and Q4 exhibit positive average slopes. The negative slope in sectors Q1 and Q2 indicate that the map point wall is moving in contraction, while the positive slopes in sectors Q3 and Q4 indicate that the map point wall is moving toward relaxation. Alternatively, an average n-point slope can be calculated in each sector, such that if the average slope is above a certain threshold, the sector would be considered in contraction or relaxation. If the overall amount of movement is less than a select threshold (i.e. 1 mm), the method may characterize the map point to have remained stationary or akinetic, in which no direction can be assigned, for the associated sector. Optionally, the system could also use slope to assess the magnitude relative to select thresholds or other map points. If the magnitude of the slope is small (relatively), there is little movement/contraction and if it is large (relatively), there is a lot of movement/contraction relative to select thresholds or other map points.

At 110, the method calculates a measure of how many map points of the wall are at least one of i) moving in a select direction and ii) moving by a select amount, during at least a portion of the phases of the cardiac cycle iii) exhibiting a strain waveform moving in a common direction (increasing or decreasing) during select phases of the cardiac cycle and/or iv) exhibiting a select extent of strain during the select phases. The direction information is found for a select total number of map points. The total number of map points may correspond to the total (or usable) number of map points in a select region of the heart, such as on the LV wall, RV wall, posterior or anterior region of the heart and the like. The total number of map points may represent the map points on one or more select walls (e.g., on pairs of opposite walls). Optionally, the total number of map points may represent the collection of points along a vein (e.g., the coronary sinus) that receives the mapping tool.

The method may permit the user to select the regions, segments, walls or veins to include in the total number of map points used to identify dyssynchrony. Optionally, the selection may be automatic, such as when it is desirable to compare certain regions, such as a comparison of lateral versus septal regions/segments, anterior versus posterior regions/segments, interior versus posterior anticeptal regions/segments and the like.

The method determines the number of points moving in an appropriate direction for the corresponding sector (e.g., phase of the cardiac cycle). For example, the appropriate/correct direction during a particular phase of the cardiac cycle may depend on whether the corresponding chamber of the heart is in a systole or diastole state. The periods of systole and diastole can be determined in several ways: (a) systole can simply be considered as ⅓ of the cardiac cycle, (b) systole can be determined as the time between the R wave and the time when motion points on the map are closest to each other, (c) as the time between the R wave and the time when motion points on the map are closest to the LV apex, or (d) as the time between the R wave and the time when motion points on the map are closest to the central axis that extends from the LV apex to the mitral annulus or middle of the LV base.

When the radial component of the movement is of interest to characterize a level of dyssynchrony/synchrony, the analysis may characterize the map point(s) of interest in the LV to have good or high synchrony when a predetermined number or percentage (e.g., at least 20 map points, a majority, 75%, most) of the map points exhibit inward (relative to the central axis of the heart) movement during the systolic phases and a predetermined number or percentage (e.g., at least 20 map points, a majority, 75%, most) of the map points exhibit outward (relative to the central axis of the heart) movement during the diastolic phases.

Optionally, the longitudinal component of movement may be used to characterize a level of synchrony or dyssynchrony. When the longitudinal component is used, the analysis may characterize the map point(s) of interest in the LV to have good or high synchrony when a predetermined number or percentage (e.g., a majority, 75%, most) of the map points exhibit downward movement (towards the apex) during the systolic phases, and a predetermined number or percentage (e.g., a majority, 75%, most) of the map points exhibit upward movement (towards the base) during the diastolic phases. When the map points of interest are in the RV, LA or RA, good or high synchrony may be exhibited with different inward, outward, upward or downward movement in associated sectors of the motion waveform 300.

If 3-D motion is used, most of the map points of the LV, during systole, should move toward the central axis of the heart that extends from the apex to the mitral annulus and/or towards the apex. During diastole, the LV wall map point(s) should move in the reverse direction. Optionally, regarding strain, during systole, most of the map points of the LV in some subset of area or volume should exhibit movement towards more negative strain (reduction in distance/area/volume). During diastole, most of the map points of the LV in some subset of area or volume should exhibit movement toward positive strain (expansion in distance/area/volume).

Figure 4:
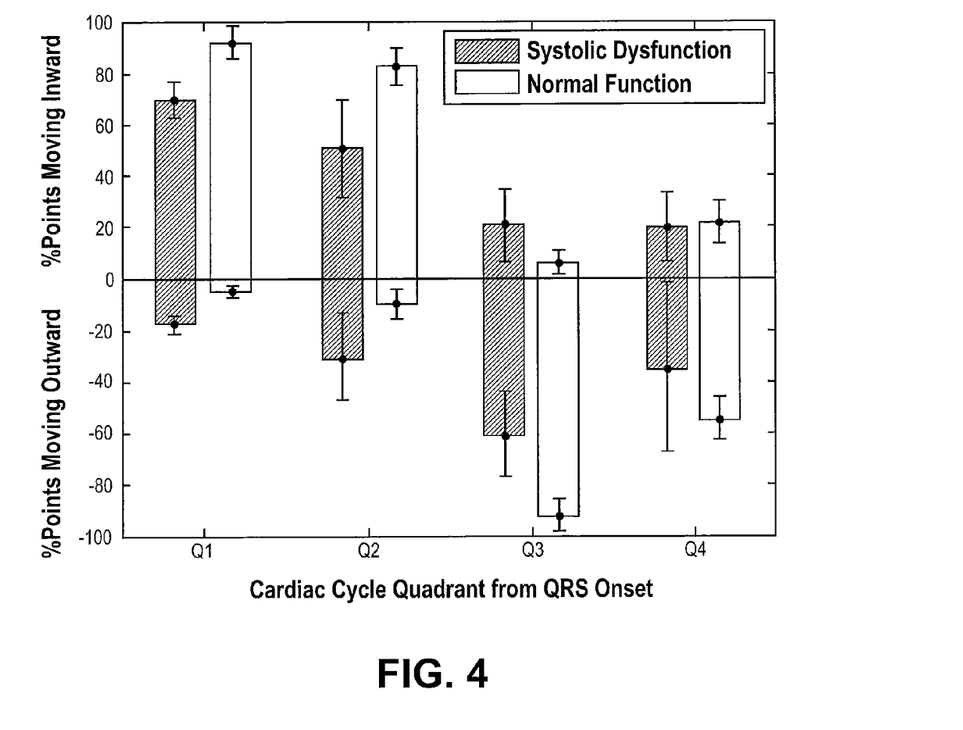
FIG. 4 illustrates a graphical presentation on a workstation of a clinician, in accordance with embodiments herein.

FIG. 4 shows radial motion data from 6 patients, three with normal systolic function and three with systolic dysfunction. The patients with normal systolic function had the majority of points moving inward during the systolic phases of the cardiac cycle (Q1 and Q2) and moving outward during the diastolic phases (Q3 and Q4). In contrast, the systolic dysfunctional patients exhibited a significant proportion of wall map point points moving outward during the systolic phase and moving inward during the diastolic phase. The systolic dysfunctional patients also exhibited a large portion of wall map point points without an assigned direction (not shown in plot), which indicates that the wall map point points did not exhibit sufficient movement to be labeled.

At 112, the method calculates and displays, on a workstation, indicia indicative of a synchrony or dyssynchrony score. The score indicia may be displayed to the clinician as one or more numeric values, a color coded scheme, one or more symbols and the like. The score indicia may be formatted as a single number, a series of numbers, colors, symbols in a table, superimposed on an image and the like. The dyssynchrony score could be calculated in many ways. In one embodiment, the score may be calculated as the mean ratio over all of the map points of i) the number of map points moving in the appropriate direction ii) to the number of map points moving in the inappropriate direction; iii) a number of map points having a common direction of strain waveform (increasing or decreasing) during select phases of the cardiac cycle and/or iv) a number of map points having a select extent of strain during the select phases.

For example, using radial motion and 4 sectors, as above, if a patient had 60% of the map points moving inward during Q1, 45% of the map points moving inward during Q2, 60% of the map points moving outward during Q3, and 50% of the map points moving outward during Q4, the dyssynchrony index would be (0.6+0.45+0.6+0.5)/4=0.54. A synchronous heart would have an index close to 1. A dyssynchronous heart would have a lower index. Alternatively, the index could be the ratio of i) inward map points to ii) the sum of outward and inward map points during the systolic phase or the ratio of i) outward map points to ii) the sum of outward and inward map points during the diastolic phase, or the average of the above two ratios. The closer the ratio to 1, the more synchronous the contraction.

Optionally, a similar score may be based on strain. When based on strain, the method calculates a percent of area (relative to a larger area) covered with strain moving towards more negative numbers during systole and a percent of area (relative to a larger area) with strain moving towards more positive numbers during diastole.

The resultant determination of dyssynchrony may be presented to the user in various manners as explained herein. To inform the user of dyssynchrony, indicia indicative of synchrony/dyssynchrony may be displayed as a single score or in connection with different times and/or different regions of the heart. The indicia may simply represent a final number or score indicating a general dyssynchrony of the entire heart, or for a select region of the heart or for one or more segments of the heart. The indicia may be a numeric value, a color, a symbol and the like. Optionally, the indicia may include separate numeric values, colors or symbols for different regions or segments of the heart.

Figure 5A:
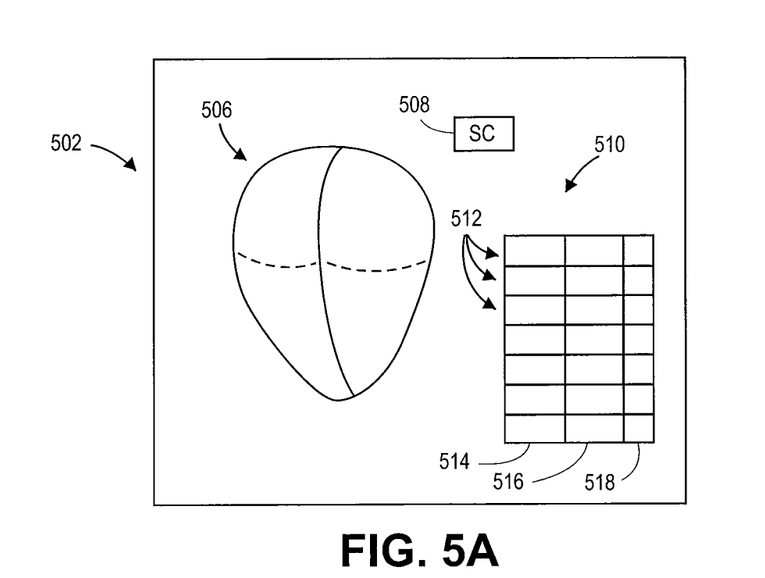

FIG. 5A illustrates an example of a display window 502 that may be presented to one or more users on a workstation, imaging system, laptop computer, smart phone, mobile handheld devices and the like. The window 502 illustrates one or more 2D or 3D images 506 of a heart, and an overall score indicia 508 as a numeric value (e.g., between 1 and 20). The window 502 also illustrates a table 510 having rows 512 associated with different regions of the heart (e.g., segments, wall regions, valves, select anatomy and the like). The table 510 includes a column 514 identifying the corresponding region, a column 516 with the score indicia, and secondary information column 518. The secondary information column 518 may provide more information regarding where or how the score indicia were determined.

Figure 5B:
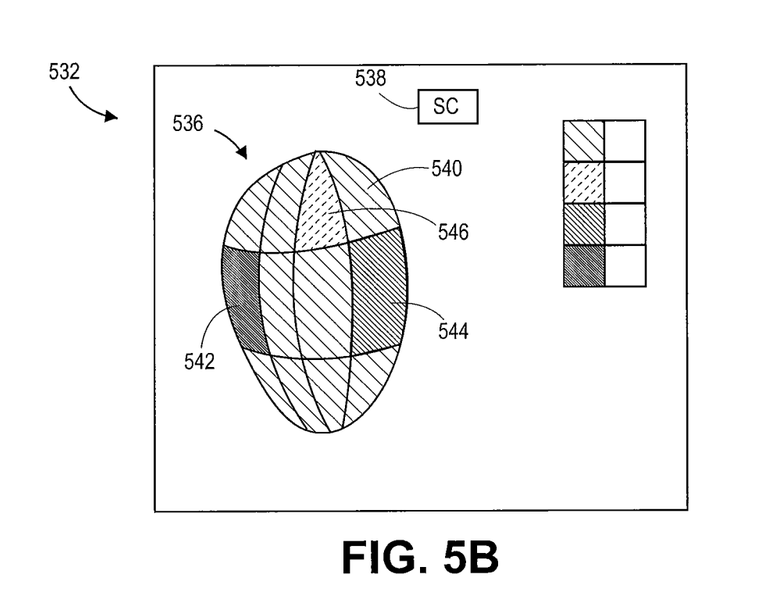

FIG. 5B illustrates an example of a display window 532 that may be presented to one or more users on a workstation, imaging system, laptop computer, smart phone, mobile handheld devices and the like. The window 532 illustrates one or more 2D or 3D images 536 of a heart, and an overall score indicia 538 as a symbol (e.g., + for leading a reference timing, "*" for acceptable, "−" lagging the reference timing). The window 532 also superimposes score indicia, presented as color coding, on the 2D or 3D image. The score indicia are illustrated as shaded areas 540 associated with one or more segments of the heart. A key 542 is illustrated to indicate a level or range associated with the shading or color coding. In the example of FIG. 5B segment 546 may slightly lead (in timing) the reference time, while segment 544 exhibits leading timing by a greater amount than segment 546. Segment 542 may exhibit substantial dyssynchrony, such as exhibiting lagging timing that exceeds an outer threshold of acceptable lag.

Optionally, the indicia may be presented in combination with one or more 2D or 3D images of the heart or the relevant region(s) or segment(s) of the heart. For example, the indicia may be displayed next to, or on, the related portions of the 2D or 3D image(s) of the heart region or segment. Optionally, the indicia may be superimposed on one or more 2D slices or 3D renderings of imaging data obtained through ultrasound, MR, CT, PET, SPECT or other imaging system. The image data may be converted into a rendered image, an animation, such as a video loop of the heart (or a portion of the heart) while moving through one or more cardiac cycles (or one or more portions of a cardiac cycle). A 3D animation may be used to show how areas of the heart move out of synchrony.

The indicia may be superimposed in various manners on the images, such as in a "venogram" where an image is presented for one or more veins (or a portion of the heart). The image has superimposed thereon color coding in regions along the vein to indicate an amount of synchrony or dyssynchrony. The colors may be indicative of a difference between the motion timing at a select region and a median timing for the reference portion of the heart. The color coding may correspond to a standard deviation of the motion timing at the select region relative to the median timing for the reference portion.

As one example, a reference point or time may be selected, automatically or by the physician. The remaining map points are then measured relative to the reference point/time. For example, the reference point may represent the septum. Alternatively, the reference time may represent an average magnitude or direction of motion. The color, number or other indicia indicative of synchrony may be assigned relative to the reference point or time. For example, when a region has a magnitude or direction of motion that lags or leads a remainder of the heart, the lagging or leading region may be assigned a color indicative of a lagging or leading behavior. Different colors may be used to indicate an amount of lag or an amount of lead. As a further example, when a portion of a vein is located along tissue that is lagging or leading a remainder of the heart in a motion characteristic of interest, the leading/lagging portion of the vein is colored uniquely or has a numeric value or symbol located thereon (or adjacent thereto).

Optionally, the indicia may include a gradation of synchrony with respect to the reference point/time(s). The gradation may represent an amount or extent to which the map points are out of synchrony with the reference time/point(s). For example, the gradation may indicate how far out of alignment one or more map points are relative to a reference location (e.g., the septum) or reference time (e.g., average motion).

Optionally, the indicia may indicate an amount of strain or strain rate experienced at the map points (or regions of interest).

Optionally, the method may determine an amount of strain or strain rate experienced at each map point. The method would determine strain or strain rate by comparing movement between two or more map points to determine how the map points move relative to one another. Once the relative motion is characterized between the map points, the method would determine an extent to which the tissue between the corresponding map points is undergoing compression or tension. The degree or amount of compression or tension can be quantified relative to other regions of the heart. The strain may then be displayed through indicia as discussed herein, such as through numeric values, color coding, symbols and the like.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc, are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

What is claimed is:

1. A method for analyzing motion data collected by a cardiovascular navigation system to determine a level of mechanical dyssynchrony exhibited by a heart, the method comprising:

obtaining a motion data (MD) set that includes a plurality of map point specific motion data (PSMD) collections of motion data, wherein the motion data in each PSMD collection includes information indicating an amount and direction of motion that occurred at a corresponding map point on a wall of the heart during a select period of time;

dividing the PSMD collections of data into sectors associated with corresponding sectors within the select period of time;

analyzing the sectors of the PSMD collections to determine at least one of a magnitude and a direction of motion at the corresponding map point of the wall of the heart during the associated sectors;

assessing at least one of the magnitude and direction of motion occurring at the corresponding map points of the wall; and calculating a measure of dyssynchrony in the map points of the wall based on at least one of i) whether the map points move in a select direction during select sectors, ii) whether the map points move by a select amount during the select sectors, iii) a direction of strain waveform during select phases of the cardiac cycle and/or iv) an extent of strain during the select phases.

2. The method of claim 1, wherein the calculating determines, as the measure of dyssynchrony, a proportion of the map points that are moving in the select direction which represents a direction of contraction during a systole phase and a direction of relaxation during a diastole phase.

3. The method of claim 1, wherein the calculating operation includes calculating, as the measure, a proportion of a number of map points that move in the select direction out of a total number of map points sampled across the heart, wherein the total number of map points may correspond to one or more of select regions, segments of opposite walls or a collection of points along a vein.

4. The method of claim 1, wherein the assessing operation is performed during at least a portion of a phase of a cardiac cycle.

5. The method of claim 1, further comprising displaying, on a workstation to a physician, a dyssynchrony score based on the measure of dyssynchrony in connection with at least one of lead placement for a cardiac resynchronization therapy (CRT) device or programming optimization for a CRT device.

6. The method of claim 1, wherein the map points of interest represent the left ventricular wall.

7. The method of claim 1, wherein the select period of time represents at least one cardiac cycle.

8. The method of claim 1, wherein the sectors correspond to phases of a cardiac cycle.

9. The method of claim 1, wherein the calculating operation measures the dyssynchrony based on at least one of i) whether the map points move in a select direction during select sectors, ii) whether the map points move by a select amount during the select sectors, iii) a direction of strain waveform during select phases of the cardiac cycle and/or iv) an extent of strain during the select phases.

10. A system for analyzing motion data collected by a cardiovascular navigation system to determine a level of mechanical dyssynchrony exhibited by a heart, the system comprising:

an input configured to receive a motion data (MD) set that includes a plurality of map point specific motion data (PSMD) collections of motion data, wherein the motion data in each PSMD collection includes information indicating an amount and direction of motion that occurred at a corresponding map point on a wall of the heart during a select period of time; and a processor configured to:
divide the PSMD collections of data into sectors associated with corresponding sectors within the select period of time;

analyze the sectors of the PSMD collections to determine at least one of a magnitude and a direction of motion at the corresponding map point of the wall of the heart during the associated sectors;

assess at least one of the magnitude and direction of motion occurring at the corresponding map points of the wall; and calculate a measure of dyssynchrony in the map points of the wall based on at least one of i) whether the map points move in a select direction during select sectors, ii) whether the map points move by a select amount during the select sectors, iii) a direction of strain waveform during select phases of the cardiac cycle and/or iv) an extent of strain during the select phases.

11. The system of claim 10, wherein the processor determines, as the measure of dyssynchrony, a proportion of the map points that are moving in the select direction which represents a direction of contraction during a systole phase and a direction of relaxation during a diastole phase.

12. The system of claim 10, wherein the processor is configured to calculate, as the measure, a proportion of a number of map points that move in the select direction out of a total number of map points sampled across the heart, wherein the total number of map points may correspond to one or more of select regions, segments of opposite walls or a collection of points along a vein.

13. The system of claim 10, wherein the processor is configured to perform the assessing operation during at least a portion of a phase of a cardiac cycle.

14. The system of claim 10, further comprising a workstation having a display configured to display a dyssynchrony score based on the measure of dyssynchrony in connection with at least one of lead placement for a cardiac resynchronization therapy (CRT) device or programming optimization for a CRT device.

15. The system of claim 10, wherein the map points of interest represent the left ventricular wall.

16. The system of claim 10, wherein the select period of time represents at least one cardiac cycle.

17. The system of claim 10, wherein the sectors correspond to phases of a cardiac cycle.

18. The system of claim 10, wherein the processor is configured to measure the dyssynchrony based on at least one of i) whether the map points move in a select direction during select sectors, ii) whether the map points move by a select amount during the select sectors iii) a direction of strain waveform during select phases of the cardiac cycle and/or iv) an extent of strain during the select phases.

19. The system of claim 10, wherein the processor is configured to calculate, as the measure, a proportion of an area or volume that moves in the select direction out of a total area or volume sampled across the heart, wherein the area or volume may correspond to one or more of select regions, segments of opposite walls or a collection of points along a vein.

* * * * *